(12) United States Patent
Ichida et al.

(10) Patent No.: US 9,901,273 B2
(45) Date of Patent: Feb. 27, 2018

(54) BIOELECTRODE

(71) Applicant: I MEDEX CO., LTD., Hanamigawa-ku, Chiba-shi, Chiba (JP)

(72) Inventors: Shinshichi Ichida, Chiba (JP); Makoto Ichida, Chiba (JP); Takashiro Minowa, Chiba (JP); Norio Nagahama, Chiba (JP)

(73) Assignee: I MEDEX CO., LTD., Chiba-Shi, Chiba (JP)

( * ) Notice: Subject to any disclaimer, the term of this patent is extended or adjusted under 35 U.S.C. 154(b) by 500 days.

(21) Appl. No.: 14/412,120

(22) PCT Filed: Jul. 3, 2013

(86) PCT No.: PCT/JP2013/068302
§ 371 (c)(1),
(2) Date: Dec. 30, 2014

(87) PCT Pub. No.: WO2014/007307
PCT Pub. Date: Jan. 9, 2014

(65) Prior Publication Data
US 2015/0173639 A1    Jun. 25, 2015

(30) Foreign Application Priority Data
Jul. 4, 2012  (JP) ................................ 2012-150956

(51) Int. Cl.
*A61B 5/04* (2006.01)
*A61B 5/0408* (2006.01)
(Continued)

(52) U.S. Cl.
CPC .......... *A61B 5/0408* (2013.01); *A61B 5/0478* (2013.01); *A61B 5/0492* (2013.01);
(Continued)

(58) Field of Classification Search
CPC .... A61B 5/0492; A61B 5/0478; A61B 5/0408
(Continued)

(56) References Cited

U.S. PATENT DOCUMENTS

2008/0281180 A1* 11/2008 Choe .................. A61B 5/04085
600/391
2008/0312524 A1  12/2008 Solosko et al.
(Continued)

FOREIGN PATENT DOCUMENTS

JP      H05-070552 U     9/1993
JP      2005-027992 A    2/2005
(Continued)

OTHER PUBLICATIONS

Notice of Reasons for Rejection of Japanese Patent Office (5 pages).
International Search Report for PCT/JP2013/068302 (2 pgs.).

*Primary Examiner* — Amanda Patton
*Assistant Examiner* — Philip C Edwards
(74) *Attorney, Agent, or Firm* — Bruzga & Associates; Charles E. Bruzga; Shlomo S. Moshen (57) ABSTRACT

The object of the invention is to provide a biomedical electrode which enables a user to easily attach by oneself without making any mistake with no specialized knowledge being required. This object can be solved by a biomedical electrode used for transmitting electrostimulation to a biomedical electrode used for transmitting electric stimulations to a biological body, for sensing electric signals from a biological body, or for both, by contacting said biomedical electrode to the biological body, in which said biomedical electrode comprises: a base material 16 formed into a sheet-shape; electrode parts 20 provided on any one surface of said base material 16; electrolyte layers 34 covering said electrode parts 20; terminal parts 30 exposed on the opposite surface to the surface on which said electrode parts 20 are provided, being electrically connected with said electrode (Continued)

parts 20, wherein said base material 16 is shaped into a form having an upper part and a bottom part wider than the upper part, so called a spread-toward-the bottom-shape, and wherein said each of the electrode parts 20 are placed at positions near the bottom of said base material 16 with the predetermined distance between every electrode parts in the width direction of the base material 16.

5 Claims, 7 Drawing Sheets

(51) Int. Cl.
*A61B 5/0478* (2006.01)
*A61B 5/0492* (2006.01)
*A61N 1/04* (2006.01)
*A61B 5/00* (2006.01)

(52) U.S. Cl.
CPC .......... *A61B 5/4836* (2013.01); *A61N 1/0472* (2013.01); *A61N 1/0496* (2013.01)

(58) Field of Classification Search
USPC ............................................... 600/393
See application file for complete search history.

(56) References Cited

U.S. PATENT DOCUMENTS

| | | |
|---|---|---|
| 2009/0157149 A1 | 6/2009 | Wahlgren et al. |
| 2012/0071731 A1 | 3/2012 | Gottesman |
| 2012/0306662 A1 | 12/2012 | Vosch et al. |
| 2013/0226275 A1* | 8/2013 | Duncan ................ A61N 1/0492 607/152 |

FOREIGN PATENT DOCUMENTS

| | | |
|---|---|---|
| JP | 2007-525269 A | 9/2007 |
| JP | 2009-518153 A | 5/2009 |
| JP | 2011-505981 A | 3/2011 |

* cited by examiner

BIOELECTRODE

The present invention relates to an electrode to be placed on a biological body to obtain biological signals, or to perform various medical treatments (hereafter, referred to as "bioelectrode"), in particular, relates to a bioelectrode suitable for a portable biological information processing device with which an individual person easily measure the biological information such as, in particular, electrocardiography, cardiac beats, motions of the body, and body temperatures.

BACKGROUND OF THE INVENTION

A portable biological information processing device has been used as a small device with which an individual person easily measure the biological information such as electrocardiography, cardiac beats, motions of the body, and body temperatures. Such a portable biological information processing device uses the biological information by, for example, that biological signals are obtained via a bioelectrode, the obtained biological signals are transmitted to a personal computer through a wireless means, or stored in a semiconductor storage, such as a memory card, which is built into the device above, for reading by a personal computer through a connecting cord thereto.

By said portable biological information processing device, management of the user's physical condition, monitoring home medical care for aged persons, and healthcare of lifestyle diseases prevention can be carried out by monitoring the biological information by the personal computer and the like, in particularly, a dedicated bioelectrode is used to obtain the electrocardiograms and the cardiac rates of the biological information.

In the prior art, Patent Literature 1 (Japanese Patent Laid-Open Publication No 2007-525269), a wearable radio unit (a portable biological information processing device) for detecting and analysing physiological data, and for transmitting the obtained condition data is proposed, in which said unit is formed such that the device can be attached by an adhesive mode to a wearer.

This Patent Literature 1 propose the wearable unit being for detecting, processing, analysing, and informing the predetermined body condition of a body, and comprising a plurality of electrodes comprising at least a pair of sensing electrodes and one referential electrode, wherein each electrode can be attached by an adhesive mode onto a body surface, and an electrode circuit module comprising a power source, and being electrically communicated with each of said plurality of electrodes, thereby processing and analysing the signals provided from said plurality of electrodes, wherein said plurality of electrodes and said electronic circuit module are covered by a single adhesive film so that the wearable unit can be adhered onto the body surface.

Furthermore, there is a bioelectrode pad to be intimately attached and fixed on skin of a biological body to transmit electric signals from the biological body to a measuring device, or to transmit electric stimulations from a stimulation device to the biological body. Regarding such a bioelectrode pad, a bioelectrode pad comprising an electrode provided on a support, and a metallic snap (hook) conducted to said electrode, wherein said pad is of a type where the pad is connected to a connector of an external device through said snap, has been used for decades.

For example, Patent Literature 2 (Japanese Utility Model Laid-Open Publication No. H05-70,552U) discloses a bio-medical electrode comprising an electrically conductive adhesive, an electronically conductive layer, a non-conductive sheet-shaped material for supporting the layer, and a means for externally connecting, in which a plurality of electrodes, being electrically independent of each other, are integrated through said sheet-shaped material.

PRIOR ART LITERATURES

Patent Literatures

Patent Literature 1: Japanese Patent Laid-Open Publication No, 2007-525269; and
Patent Literature 2: Japanese Utility Model Laid-Open Publication No. H05-70,552

SUMMARY OF THE INVENTION

Problems to be Solved by the Invention

A bioelectrode has been used for transmitting electric signals from the biological body to a measuring device, or for transmitting electric stimulations from a stimulation device to the biological body. This bioelectrode is commonly used by attaching it to the predetermined place based on the specialized knowledge.

However, there is also a case where the bioelectrode is self-attached to a body (chest part, etc.) of a person to be measured, when management of the user's physical condition, monitoring home medical care for aged persons, and healthcare of lifestyle diseases prevention are carried out. This is for that any change of the physical condition of a personal user can be immediately self-known from biological information obtained whenever, wherever, and whatever behaviour of said person in one's daily life.

It is necessary to attach the bioelectrode to the predetermined place or position on the body, even when the user (a person to be measured) self-attaches the bioelectrode to one's body. Therefore, it must be easily known where the bioelectrode should be placed in which orientation. In addition, said electrode can be easily attached but is difficult to detach.

Therefore, the first object of the invention is to provide a bioelectrode which enables a user to easily attach by oneself without making any mistake about the orientation or the place for the attachment with no specialized knowledge being required.

On the other hand, common measurements of cardiac diagrams include 12-lead-, limb lead-, and chest lead-measuring methods. However, these measuring methods require specialized knowledge. Furthermore, a measurement using a special electrocardiogram measuring apparatus is only available at a hospital, i.e., the measurement cannot be carried out unless a person to be measured goes to a hospital.

Means for Solving the Problems

To solve any one of the aforementioned problems, the present invention provides a small and high-performance bioelectrode to be used for transmitting electric signals from a biological body to a measuring device, or for transmitting electric stimulations from a stimulation device to a biological body, which is particularly suitable for obtaining biological signals such as electrocardiograms, electromyograms, or brain waves in a portable (wearable) biological information processing device.

That is, the present invention provides a bioelectrode used for transmitting electric stimulations to a biological body, for sensing electric signals from a biological body, or for both, by contacting said bioelectrode to the biological body, said bioelectrode comprises a base material formed into a sheet-shape; electrode parts provided on any one surface of said base material; electrolyte layers covering said electrode part; terminal parts exposed on the surface opposed to the surface on which said electrode parts are provided, being electrically connected with said electrode parts, wherein said base material is shaped in a form having an upper part and a bottom part wider than the upper part, so called a spread-toward-the bottom-shape, and wherein said respective electrode parts are placed at positions near the bottom of said base material with the predetermined distances in the width direction of the base material.

In the electrode according to the invention, the base material on which the electrode parts are provided is shaped into a form having an upper part and a lower part wider than the upper part, so called as a spread-toward-the bottom-shape. In an area of this wider-formed bottom of the base material, the electrode parts are provided. Therefore, when a plurality of electrodes is used, for example, a bioelectrode can carry out a single-lead measurement of a one channel, 2 (two) electrodes can be provided to the wider-formed part of the base material such that they are apart from each other. By this, for example, when one electrode part is a measuring point and the other electrode part is a referential point, the distance between the measuring and referential points can be taken widely. In particular, the distance between the measuring and referential points (i.e., the distance between the electrode parts) is set to be from 50 to 200 mm, preferably, 70 to 100 mm, wherein the distance between the centers of the electrode parts is measured, thereby setting large output signals, as well as, realizing minimization of the bioelectrode. Moreover, by forming the bottom side widely, an area for attaching the bioelectrode to a biological body can be also widened. Therefore, even when a biological signal processing device described below is mounted on said electrode to use, it can be secured to hold said biological signal processing device.

The aforementioned base material can be formed from an insulating material having sufficient flexibility and a certain shape retaining ability, as well as, a tensile strength of a level where the material is not easily broken. More specifically, for example, resin materials such as a polyethylene naphthalate film, a polyethylene terephthalate film, a polyamide film can be used, and materials having electrical insulating properties such as synthetic material non-woven cloths, as well. It is desired, however, that the base material is formed from a material having water resistance and waterproof properties, when the bioelectrode is used for a wearable biological information processing device, since said bioelectrode is also used in everyday life.

Particularly in the bioelectrode according to the invention, this base material is formed so as to have the upper part and the lower part wider than the upper part (a spread-toward-the bottom-shape) in the attached state. Such a shape includes a trapezoidal shape, optionally provided with a notch or a tab at any or all of the edges of said trapezoidal shape. For example, the base material may be formed into a "M"-shape having a widened bottom side, in which there are 2 (two) notches at the widened formed bottom side (the base side), and there is 1 (one) notch at the upper part (the top side). As a result, the base material can be bent in the lines connecting the notch at the upper edge and each of the notches at the lower edge.

Accordingly, the bending parts to be able to bend depending on the movement of the user during the attachment thereof are limited to regions including the lines connecting the upper and each of fate lower notches. Therefore, the electrode parts can be formed in the regions except for the bending parts. In the other words, a bioelectrode can be provided, in which the aforementioned base material is formed to have one notch at the upper side edge, and two notches at the lower side edge, wherein at least each of the electrode parts, desirably the electrode parts and the terminal parts, are provided in any region except for the regions where the lines connecting the upper notch and each of the lower notches extend. In this way, by providing the electrode parts and the like in the base material in the region except for the regions having the parts tending to be bent as the user's body moves, it can be considered to avoid any influence of noise occurred as the user's body moves, and to stably obtain biological information.

Furthermore, when notches or tabs are formed at the edges of the base material, as described above, it is desirable that the notches or tabs are shaped with a curvature, i.e., not having any angled corner. By shaping the notches or tabs in this way, hurting the body can be avoided, even if a bent part contacts to the body.

Said electrode parts are formed on any one of surfaces of the base material by using an electrically conductive material. These electrode parts can be formed by any material having electric conductivity. It is desirable, however, that the base material can be formed by printing or applying an electrically conductive material, for example, carbon, metals, metal compounds, or a mixture of carbon and metal or metal compounds. When each electrode part is formed to have a small area from 18 mm$^2$ to 100 mm$^2$, a bioelectrode having a specifically excellent electrocardiopraphic waveform rise property can be provided.

On the other surface side of the base material, there are the terminal parts which are electrically connected to these electrode parts. For the electric connections between the electrode parts and the terminal parts, electric wires may be used. In order to improve manufacturability, i.e., make it easy to manufacture, eliminate uncomfortable feeling while attaching to a biological body, or reduce in weight, it is desirable to form the electric connections with wired parts provided by printing or applying the electric conductive material. Also, it is necessary that at least any one part of the terminal part passes through the base material so as to expose be exposed on the surface on which the electrode part is present, wherein the electrically conductive material layer can be formed such that said exposed part is electrically connected to said electrode part.

The terminal parts can be formed by metallic materials. The terminal part can be formed into a shape comprising a flat surface part to be present on the surface on which the electrode parts are provided in the base material, and an axis part starting from said flat surface and extending by passing through the base material. For example, the terminal part can be shaped into a "convex"-shape or an "L"-shape in the longitudinal section. When the terminal part is formed in this way, the wiring parts formed by printing or applying the electrically conductive material can be formed into a line or a band shape, which electrically connect between the electrode parts and the flat surface parts of the terminal parts. Also, an electrically conductive cover can be provided on the axis parts extending by passing through the base material, in order to avoid breaking out the base material, thereby preventing said terminal parts from dropping out.

The number of combination unit of the electrode parts, the terminal parts and the wire connections therebetween can be of one or two or more per base material. However, a bioelectrode for a single-lead measurement of one channel, it is desirable to provide two combinations thereof in view of ease of attachment to a biological body, since two electrodes (a measuring point and a referential point) can be provided at the same time by attaching one bioelectrode.

When two electrode parts are provided on one base material in this way, it is desirable that each electrode part is provided at a place closed to the edge of the base material in the width direction, whereby a long distance between the measuring point and the referential point can be obtained so that large output signals can be set. In this case, two terminal parts, corresponding to each electrode part, are provided. It is desirable that each of these terminal parts is provided next to each other at a position close to the center of the base material in the width direction. The reason why is that by shortening the distance between the terminal parts, a small portable (wearable) biological information processing device can be mounted thereon.

In the bioelectrode provided with 2 (two) electrode parts and 2 (two) terminal parts in the way as described above, the terminal parts and the electrode parts present in the areas of both sides of the base material in the width direction are electrically connected with each other by wiring parts. For the wiring parts, though electric conductive wires can be used, it is desirable to form said parts by printing or applying, in order to facilitate the manufacturability or to eliminate uncomfortable feeling while attaching to a biological body.

Particularly in the bioelectrode according to the invention, it can be achieved that a large distance between the electrode parts is provided in the way as described above, while the terminal parts can be relatively closely provided each other. For example, the distance between the terminal parts can be about 10 mm to 100 mm, preferably, about 15 mm to 50 mm. By providing the distance between the terminal parts in this way, it is possible to establish the connection therebetween even in small portable (wearable) biological information processing device having a short distance between terminals. The reason why any distance between the terminal parts or the electrode parts can be set in the invention is that the electrode parts and the terminal parts are separately provided, and both parts are connected electrically by wiring parts.

On the surface of the base material where the electrode parts are present, the electrode parts and the terminal parts are covered by electrolyte layers. The electrolyte can be provided such that (1) each pair of the electrode part and the terminal part connected each other by a wiring part is covered; or (2) each electrode part is covered.

In other words, every combination of the electrode part and the terminal part connected by the wiring part can be covered separately by the electrolyte layers. For example, a first electrolyte layer region covering one pair of the electrode part and the terminal part present in one side of the base material in the width direction (horizontal direction), and a second electrolyte layer region covering the other pair of the electrode part and the terminal part present in the other side of the base material in the width direction can be provided. In this case, the first and the second electrolyte layer regions are provided such that they are not electrically connected with each other. By covering the electrolyte layers, biological signals can be obtained by the electrode parts via the electrolyte layers contacting to the biological body. Therefore, it is necessary that the electrolyte layers regions are not electrically connected with each other in order to avoid any short of the electrode parts.

In a bioelectrode provided with two or more of pairs of the electrode part and the terminal part connected by the wiring part in the base material, it is possible that at least every electrode part is covered separately by respective electrolytes, i.e., a first electrode electrolyte layer region covering one electrode part, and a second electrode electrolyte layer region covering the other electrode part are formed. These first and the second electrode electrolyte layer regions are formed such that they are not electrically connected with each other.

Since said electrolyte layers to be contacted to a biological body and have functions such as of transmitting biological signals to the electrodes, they are made from materials at least having electric conductivity. It is desirable that the electrolyte layers are formed by materials having flexibility or elasticity in order to increase adhesiveness to the biological body, and they can be also formed from materials having semifluidity or fluidity, such as gel like or gelatinous materials. Whereby, the electrolyte layers can be composed of electrically conductive resin materials such as acrylic resins to which electric conductivity have been imparted, and urethane resins to which electric conductivity have been imparted, as well as, karaya gum to which electric conductivity has been imparted. Furthermore, it is desirable that the electrolyte layers have certain adhesiveness such that they can be adhered to the biological body.

Moreover, it is desirable to provide a shield layer comprised by an electrically conductive material in the bioelectrode according to the invention. For example, the shield layer made of an electrically conductive material can be provided on the surface of the base material on which the terminal parts are present (i.e., the opposite surface of the surface on which the electrode parts are present). Since biological signals from the biological body such as cardiac electric signals and heart-rate signals are considerably, affected by noises such as electromagnetic waves or electricity (static electricity, etc.) from the internal or external biological body. Therefore, as a countermeasure against the harmful affection by the noises a shield is provided to reduce noises from the internal and the external human body. Such a shield layer can be formed by using an electrically conductive material, for example, carbon, metals or metal compounds, or mixtures of carbon and metals or metal compounds can be used.

It is desirable that the shield layer is grounded in order to stabilize the potential, i.e., it is desirable to construct the shield layer to be grounded on the biological body. In the bioelectrode according to the invention, it is desirable that the shield layer is electrically connected with a third electrolyte region in the electrolyte layers contacting with the biological body. In this case, the shield layer is not electrically contacted with the first or the second electrolyte region, or any electrolyte connecting with the electrode part or the terminal parts. As a result, the difference of the potential between the shield layer and the biological body can be minimized, and therefore the potential of the shield layer is stabilized, thereby more increasing the shield effect.

Though the electric connection structure between the shield layer and the third electrolyte region is not specifically limited, for example, throughholes are provided to the base material, and an electrically conductive material to form the shield layer is printed or applied such that the material enters the throughholes. From the opposite side surface of the side surface on which the shield layer is provided, the electrically conductive material is printed or applied such that the material enters the throughholes in the base material, thereby establishing electric connections between the conductive materials present on both sides of the base material. The electrically conductive material provided on the opposite surface of the surface on which the shield layer is provided is contacted with the biological body, directly or indirectly via the third electrolyte region, and the shield layer therefore can be grounded on the biological body.

In this way, in order to electrically connect the shield layer with the third electrolyte region, it is desirable that there is an earth connection part provided by printing or applying the electrically conductive material on the opposite surface of the surface on which the shield layer is provided in the base material (i.e., the surface on which the electrode parts are provided in the base material). By providing such an earth connection part, it can be ensured to establish the electric connection with the shield layer, and to enlarge the contact area surface with the third electrolyte region, thereby certainly grounding the shield layer on the biological body.

In order to solve at least any one of the aforementioned problems, the invention provides a biological signal measuring device applying said bioelectrode.

That is, the biological signal measuring device comprises a bioelectrode comprising a base material shaped into a sheet form, electrode parts provided on any surface of said base material, electrolyte layers covering said electrode parts, and terminal parts exposed on the opposite surface of the surface on which the electrode parts are provided in the base material to connect with said electrode parts; and a biological signal measuring device main unit for obtaining signals from said bioelectrode, which is characterized in that said bioelectrode is the bioelectrode according to the invention.

The biological signal measuring device main unit used in the biological signal measuring device may be a portable (wearable) biological information processing device for simply performing the measurement of biological information such as electrocardiograms, heart rates, body motions, or body temperatures by an individual person. Said portable (wearable) biological information processing device is constructed so as to obtain biological signals via the bioelectrode, transmit the obtained biological signals to a personal computer through a wires means, or to store said signals in a semiconductor memory device such as a memory card installed in said device so that the signals can be transmitted to the personal computer.

It is desirable to establish the connection between the bioelectrode and the biological signal measuring device by using an attach/detach means by means of hooks or terminals, thereby facilitating the connection.

In the aforementioned biological signals measuring device, biological signals can be obtained more precisely due to the use of the bioelectrode according to the invention described above. In particular, when using the bioelectrode provided with the shield layer, the biological signals having the reduced bad influence by noises from the internal and the external body can be obtained.

Effect of the Invention

In the bioelectrode according to the invention described above, the bottom part is widened to shape. This provides a bioelectrode which can be easily attached by a user oneself having no specialized knowledge required without making any mistake. Therefore, the bioelectrode can be directly attached by a user oneself to one's chest part to use, even when said bioelectrode is used for the management of the user's physical condition, monitoring home medical care for aged persons, and healthcare of lifestyle diseases prevention. Accordingly, the bioelectrode can be used also in a portable (wearable) biological information processing device, and thus any change of the physical condition of a personal user can be immediately self-known from the biological information obtained whenever, wherever, and whatever behaviour of said user in one's daily life.

Providing two (2) electrode parts per base material allows the bioelectrode to carry out a single-lead measurement of one channel, thereby realizing a small and high-performance bioelectrode which can be attached by a user oneself in one time. Therefore, a bioelectrode that can be attached by a user oneself to one's body without going any hospital for a specialized electrocardiogram measuring machine can be implemented.

EMBODIMENT OF THE INVENTION

The bioelectrode according to the invention will now be explained with reference to the drawing below. Particularly in the embodiments of the invention, examples of bioelectrodes which are suitable to use in a portable (wearable) biological information processing device are provided. In these bioelectrodes are formed into a "M"-like shape having a widened bottom side. As a matter of convenience, the bioelectrode according to the invention is explained with said bioelectrode, in which the ide facing to the biological body is the body surface side, and the side facing outward is the outer surface side.

Figure 1:
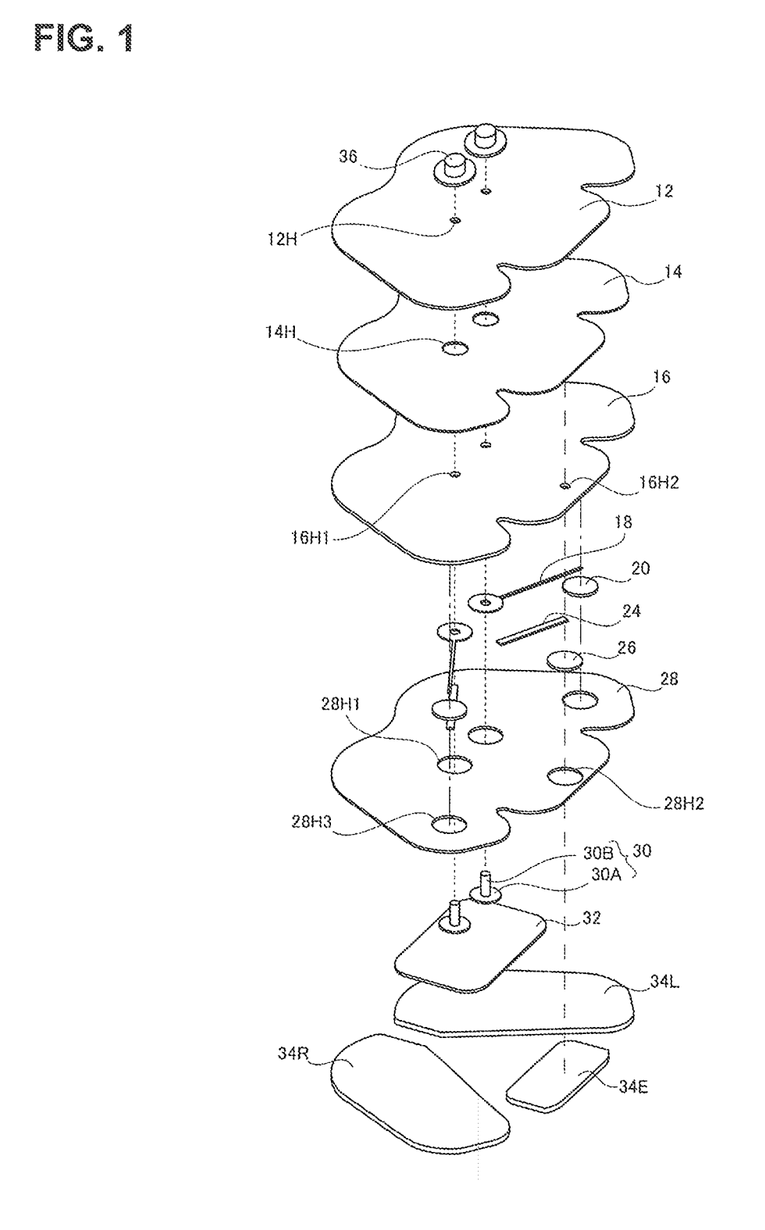
FIG. 1 shows an exploded perspective view of a bioelectrode of one embodiment according to the invention.

FIG. 1 is an exploded perspective view of a bioelectrode according to the invention, on the outer surface side showing the upper of a base material 16 (the directions shown in the drawing are normal directions.), a shield layer 14 is layered, on which a cover film 12 comprised by a resin material is provided.

The base material 16 is a film or sheet formed by a non-electrically conductive material. On this base material 16, layers or structural elements as described below are provided. The base material 16 is formed by an insulating material, which has sufficient flexibility, at the same time can maintain a certain form, and has a tensile strength of a certain degree at where the material cannot be easily broken. For the base material 16, a polyetheylen terephthalate film (or sheet), can be used. Other films or sheets made of, for example, resin materials such as polyethylene naphthalate film (or sheet), any film or sheet made from materials having electric insulation property, such as non-woven cloths or synthetic non-woven cloths can be used for forming the base material 16. However, when the bioelectrode is used for a portable (wearable) biological information processing device, the base material is desirably formed from a resin film or a resin sheet having water resistance and waterproof properties, when the bioelectrode is used for a wearable biological information processing device, since said bioelectrode is also used in everyday life.

In the embodiments according to the invention, the base material 16 is formed into an "M"-like shape with a widened bottom side. Therefore, electrode parts 20 to be provided to the bottom side (described below) can be placed with a sufficient distance, i.e., 50 to 200 mm, preferably, 70 to 100 mm between centers of the electrode parts 20 (a measuring point and a referential point). Consequently, a large output signal can be taken. Furthermore, in the base material 16 of an "M"-like shape with a widened bottom side, both sides of the shape (the right and left sides) can form an angle from 10° to 80°, preferably, 15° to 45°. By forming such an angle between the both sides in the width direction, the base material, in which a sufficient width of the bottom side can be ensured, while a certain height for placing a small portable (wearable) biological information processing device can be ensured, can be provided. Unless otherwise specifically indicated, a shield layer 14, and a cover film 12, etc., as described below, will be formed into the same profile shape as this base material.

The shield layer 14 to be layered on said base material 16 can be formed by, for example, printing or applying an electrically conductive material onto the base material 16. In an embodiment according to the invention, since said shield layer is formed with an area that covers most of the area of the base material 16, the shield effect against electromagnetic wave-noise to the electrode parts 20 or the wiring parts 18 can be increased. When reducing the material to form the shield layer 14, however, said layer may be formed to cover at least the respective outer surface sides of the electrode parts 20 and the wiring parts 18. Alternatively, the shield layer can be formed by printing or applying a mixture of carbon and metals or metal compounds, other than carbon.

Then, the shield layer 14 is covered by a cover film 12 comprised by any suitable resin sheet. This cover film 12 covers the shield layer 14, and used for preventing the shield layer 14 from being peeled or dropped off. This cover film can be also used for printing various information, for example, product names and orientations for the use, or for decorating the bioelectrode. Such cover film 12, in addition to being integrally bonded or fused at its periphery to the periphery of the base material 16, can be integrated by adhering the shield layer 14 with an adhesive or the like.

On the lower part of the base material 16 (the body surface side), the electrode parts 20, the wiring parts 18 and an earth connection part 26 are formed by printing or applying the electrically conductive materials. These electrode parts 20, the wiring parts 18 and the earth connection part 26 can be formed by using not only the same electrically conductive material, but also different electrically conductive materials for at least one of them. In the embodiments according to the invention, the electrode parts 20 are formed with silver chloride, the wiring parts 18 and the earth connection part 26 are formed with silver. The wiring parts 18 are formed as a silver layer, and the electrode parts 20 to be electrically connected with said wiring parts 18 are formed by silver-silver chloride. The reason why the electrode parts 20 are formed by silver-silver chloride is for the ion exchange with the electrolyte layers 34. It is desirable that the silver-silver chloride layers have a mixing ratio of silver to silver chloride, silver:silver chloride, is 9:1 to 6:4 in weight ratio. By providing such silver-silver chloride layers (electrode parts 20), any polarization in the electrode parts 20 at the measurement can be avoided. Therefore, the bioelectrode of the invention is specifically desirable when it is worn for a long term, for example, a bioelectrode for a Halter monitor, and for a portable (wearable) biological information processing device. Also, the bioelectrode of the invention is specifically desirable for implementation of smooth ion exchange when introducing drugs into the body by electrifying, for example, iontophoresis treatment. In addition, however, any or every one of the electrode parts 20, the wiring parts 18 and the earth connection part 26 may be formed by various metals having electrical conductivity, such as silver-silver chloride, silver, gold, copper, carbon, aluminum, and nickel.

In the present embodiments, the wiring parts 18 are printed or applied to the base material 16, and then the electrode parts 20 are printed or applied to layer thereon, but vice versa may be acceptable in view of lamination structure. Furthermore, the respective electrode parts 20 and wiring parts 18, which have been formed by printing or applying, are electrically connected each other in the width direction of the base material 16. In other words, every pair unit of the respective wiring parts 18 and electrode parts 20 present at the left side of the base material 16, viewing from the biological body side, are electrically connected, while every pair unit of the respective wiring parts 18 and electrode parts 20 present at the right side of the base material 16, viewing from the biological body side, are electrically connected, wherein no electrical connection is established among every pair unit.

After the electrode parts 20, the wiring parts 18, and the earth connection part 26 are formed on the base material 16, an insulating part 24 comprised by a material having electrical non-conductivity (insulation property) is formed thereto. This insulating part 24 can be formed by using a photoresist material having electrical insulating property. In the embodiments of the invention, this is formed into a band-like shape so as to cover the wiring parts 18. The material to form this insulating part 24 is not specifically limited, and said part can be formed by light curable resin compositions such as novolac epoxy-type acrylate compounds, or bisphenol fluorene-type epoxy acrylate compounds, or acid denaturation substances of these epoxy acrylate compounds, as well as, thermosetting resin compositions or thermoplastic resin compositions. It is not always necessary to use the photoresist materials for this insulating part 24. For example, this part can be formed by using materials having electric insulating property, for example, vinyl chloride films (or sheets), PET films (or sheets), or synthetic material non-woven cloth, by adhering in layers.

In the embodiments of the invention, an electrolyte holding part 28 formed into the same contour shape as the base material 16 is provided after the formation of the insulating part 24 in this way. This electrolyte holding 28 adheres to the base material, and functions to firmly hold the electrolyte layers formed into a gel due to its rough surface structure. For this electrolyte holding part 28, other than said resist material, textiles, or a resin sheet/resin film having an uneven surface or formed into a mesh can be used. Particularly in the embodiments of the invention, this part is formed into a layer by printing or applying the resist material similarly to the insulating part 24 above. As a result, though in the wiring parts, two layers of the resist material are laminated, they are different from each other in the function and the required precision (print precision). Specifically, in order to surely cover the wiring parts, it is necessary to form the insulating parts into a precise dimension at a right position, while the electrolyte holding part 28 does not have to firmly cover the wiring part since said part is required only to hold the electrolyte. However, when the electrolyte holding part 28 is formed so as to firmly cover the wiring parts, it can be also considered to omit the insulating part 24 so long as the electrolyte holding part has insulating property. When the insulating part 24 is formed, the electrolyte holding part 28 does not have to have electric insulation property. Furthermore, when the surface on which the electrolyte layers are to be provided is formed into a rough surface in the base material 16 it can be also considered to omit the electrolyte holding part 28.

Terminal parts 30 are provided to electrically connect with the wiring parts 18. In the embodiments of the invention, the terminal parts 30 each comprises a disk-like flat surface part 30A, and an axis part 30B projecting from the flat surface part 30A. The flat surface part 30A passes through a hole provided to the electrolyte holding part 28 so that said part can contact with the wiring part 18. Whereby, the terminal parts 30 and the wiring parts 18 can be electrically connected with each other. The axis part 30B projecting from the flat surface part 30A successively passes through a hole 16H provided to the base material 16, a hole 14H provided to the shield layer 14, and a hole 12H provided to the cover film 12 to expose on the outside surface. The tip of the axis part 30B to be exposed on the outside surface is held by a stud 36 to prevent the terminal part 30 from dropping off the base material 16. The base material 16, the shield layer 14, and the cover film 12 are sandwiched by the flat surface part 30A of the terminal part 30 and the stud 36 to being firmly combined. Regarding the holes, the hold 14H provided to the shield layer 14 through which the axis part 30B of the wiring part 18 passes is opening with a diameter larger than that of the axis part 30B in order not to the contact at least with the axis 30B. This is to insulate the shield layer 14 from the transmission lines for the biological signals (i.e., the line electrode part 20—the wiring part 18—the terminal part 30).

The electrolyte holding part 28 is also provided with a hold 28H3 for the exposure of the electrode part 20, and a hold 28H2 for the exposure of the earth connection part 26. By providing these holds, each of the electrode part 20 and the earth connection part 26 can be contacted with the respective electrolyte layers 34, thereby carrying out the ion exchange with the respective electrolyte layers 34.

Onto this electrolyte holding part 28, an insulation film 32 is adhered so as to cover the terminal parts 3Q. This insulation film 32 prevents any short-circuit of the electric signals between the disc-like parts 30A of the terminal parts 30, as well as, between the ring parts of the wiring parts. Furthermore, in the embodiments of the invention, the base material 16 having flexibility is provided with terminal parts 30 made of metal. Therefore, the insulation part 24 which has been formed to be thin has a possibility to be cracked adjacent the metallic terminal parts 30. If the insulating part 24 is cracked, the insulation film 32 is provided in order to surely insulate between two electrode parts 20, and between two wiring parts 18. By providing such an insulation film, the base material 16 can be reinforced adjacent the metallic terminal parts 30. Therefore, when a portable (wearable) biological information processing device is provided to the terminal parts 30, said device can stably be held.

In the embodiments of the invention, the electrolyte layers 34 are laminated such that they cover one part of the insulation film. These electrolyte layers 34 are formed by using a material having electric conductivity. That is, these electrolyte layers 34 can be comprised by, for example, acrylic resins, and urethane resins, etc., and karaya gum as well. It is desirable to form these electrolyte layers 34 so as to have semifluidity or fluidity, or to be sufficiently soft.

Particularly in the embodiments of the invention, the electrolyte layers 34 comprise a first electrolyte layer region 34L which covers one pair of electrode part 20 and wiring part 18 provided on one side of the base material 16 in the width direction, a second electrolyte layer region 34R which covers the other pair of electrode part 20 and wiring part 18 provided on the other side of the base material 16 in the width direction, and a third electrolyte layer region which is electrically connected to the shield layer 14 comprised by the electrically conductive material. In particular, in the embodiments of the invention, there is no electric connection between the first electrolyte layer region 34L, the second electrolyte layer region 34R, and the third electrolyte layer region 34E is established.

With the structure as described above, at the respective parts of the base material 16 in the width direction, the terminal part 30, the wiring part 18, the electrode part 20, and the electrolyte layers 34 are electrically connected in turn, in which when this bioelectrode is attached to a biological body, the signals from the biological body will be transmitted in reverse.

The electric connection between the shield layer 14 and the earth connection part 26 can be realized by that the electrically conductive material forming the shield layer 14 is introduced to the inner wall surface of the throughhole 28H2 provided to the base material 16, while the electrically conductive material forming the earth connection part 26 provided on the opposite surface of the surface on which the shield layer 14 is formed in the base material 16 is introduced to the inner wall surface of the throughhole H2, and these materials are connected.

To realize the electric connection using such a throughhole 28H2, it is desirable to form the shield layer 14 and the earth connection part 26 are formed by screen printing, and the like. Also, it is desirable to use a material (electrically conductive material) having sufficient fluidity for the printing. Moreover, it is desirable that the throughhole 28H2 is formed to have a hole diameter more than 2 mm, preferably 3 mm or more, more preferably, 5 mm or more. By forming the throughhole having such a hole diameter, a thin-film connection circuit can be formed on the inner wall surface of the throughhole 28H2. In addition, this is also for avoiding that the thickness at the area part of the throughhole 28H2 is increased. The throughole 28H2 can be formed by any processing method, for example, drill processing, laser processing, or punching processing.

On the earth connection part 26 electrically communicating with the shield layer 14, the third electrolyte layer region is adhered to laminate. Whereby, the shield layer 14 can be earthed to the biological body to stabilize its potential, resulting in adverse effects by noises of electromagnetic waves scattering in the air can be reduced, thereby obtaining more precise biological signals.

Figure 2:
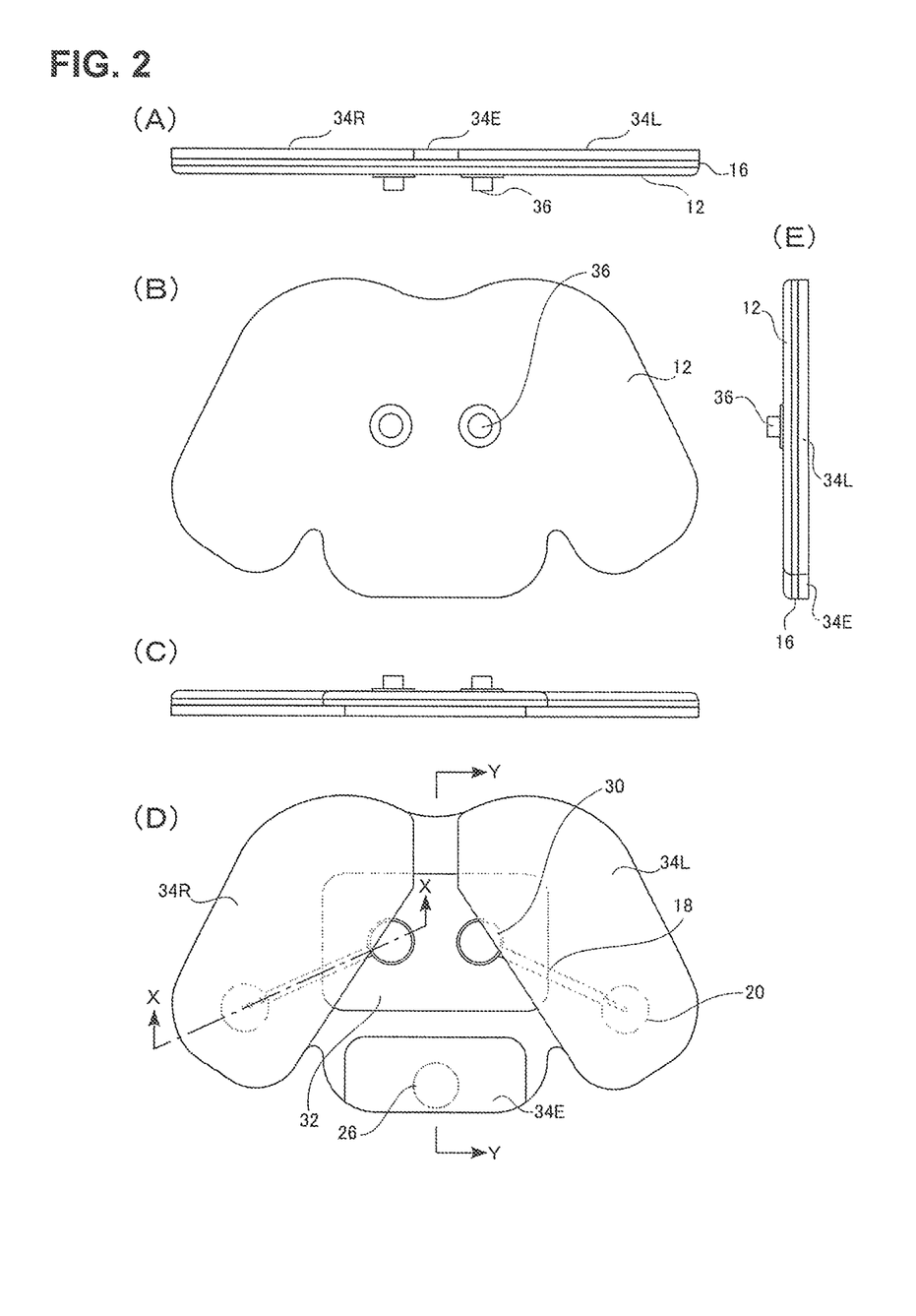
FIG. 2 shows a plane view (A), a front view (B), a bottom plan view (C), a back view (D), and a right side view (F)

FIG. 2 shows a plane view (A), a front view (B), a bottom plan view (C), a back view (D), and a right side view (E) of the bioelectrode shown in FIG. 1. In the bioelectrode shown in this drawing, the terminal parts 30, which output the obtained biological signals to a portable (wearable) biological information processing device, are aligned in the horizontal line with a certain distance but closed to each other (see plan view (A), and front view (B)). On the other hand, the electrode parts 20 are provided, being apart from each other, at the bottom part which is widely formed. Therefore, when determining that one electrode part 20 is a measuring point and the other electrode part 20 is a referential point, a long distance between the measuring point and the referential point can be obtained so that large output signals can be set.

In the embodiments according to the invention, the bottom side of the base material 16 is widely formed to assure a wide area where the electrolyte layers 34 are displaceable. Therefore, when the electrolyte layers 34 are formed by a gel having adhesive property, the adhesive strength to the biological body can be enhanced. The terminal parts 30 are provided to almost the middle part between the upper and the lower side of the base material 16 (see the front view (B) and the right side view (E)). As a result, even if a portable (wearable) biological processing information device is engaged with the terminal parts 30, the position for mounting the device can be selected to a position near the gravity center of the adhesive gel of a large are surface, thereby reducing uplift of and drop off the bioelectrode.

For easy understanding the presence of every layer, each layer shows to be thicker in FIG. 2. In practice, however, all layers are formed to be thin because they are formed by printing or applying. The result is to ensure flexibility of the bioelectrode, providing easy following up the motion of the user.

In the embodiments of the invention, since the base material 16 is formed into an "M"-like shape, i.e., a spread-toward-the bottom-shape, the parts to be bent of the bioelectrode depending on the motion of the body can be restricted to the areas including the lines connecting the upper notch and each of the lower notches provided at the edges. For actively bending these parts, as shown in FIG. 2 (D), the electrolyte layers 34 are provided along the edges of both sides of the base material 16 formed into an "M"-like shape in the width direction. Therefore, the areas to be bent depending on the motion of the body can be specified to prevent it from bending at any unintended part. Furthermore, by covering the electrode parts 20 with this electrolyte layer 34, the electrode parts 20 can be secured connecting to the biological body even if the wearer moves, thereby stably obtaining the biological signals.

Moreover, since the electrode parts 20 formed by printing or applying will be certainly contacted with the electrolyte layers 34 (the first electrolyte region 34L and the second electrolyte layer region 34R), a small area surface for every electrode part 20, e.g., ranging from 18 mm$^2$ to 100 mm$^2$, can be achieved. Thus, the bioelectrode becomes one being highly excellent in rising electrocardiogram waveforms. The electrode parts can be formed into any shape, for example, a circular shape having an outer diameter of 10 mm.

Figure 3:
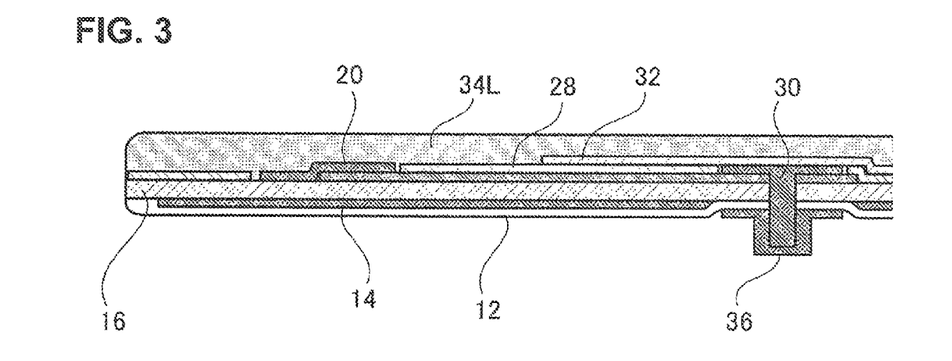
FIG. 3 shows a cross sectional view along the line X-X in FIG. 2.

FIG. 3 is a view showing a cross sectional view along the line X-X in this FIG. 2 (D). In this FIG. 3, the connecting structure of the electrode parts 20, the wiring parts 18, and the terminal parts 30, each present in the left side when viewing the bioelectrode from the biological body, is represented. As shown in FIG. 3, the wiring parts 18 are provided on the surface of the base material 16 facing to the biological body side (body surface side), and the electrode parts 20 are formed into a layer at the tips thereof. At the starting edges of the wiring parts 18 (i.e., the side where ring parts are present), the disc-like parts 30A of the terminal parts 30, passed through the hole 28H1 formed to the electrolyte holding part 28 are provided in their adhering state. The axis parts 30B of the terminal parts 30 are passed through the base material 16, the shield layer 14, and the cover sheet to project out the opposite surface, and then snapped into the studs 36. On the other hand, in the area except for the electrode parts 20, the terminal parts 30, and the earth connection part 26, the electrolyte holding part 28 comprised by an insulating material is laminated on; around the terminal parts 30 on the electrolyte holding part 28, an insulating sheet is further laminated; and then the electrolyte layers 34 are laminated thereon. The shield layer 14 provided on the opposite surface (the outer surface) of the base material 16 provides insulation from the terminal parts 30 by closely attaching the cover sheet to the base material 16 with the disc-like parts 30A of the terminal parts 30 and the studs 36.

Figure 4:
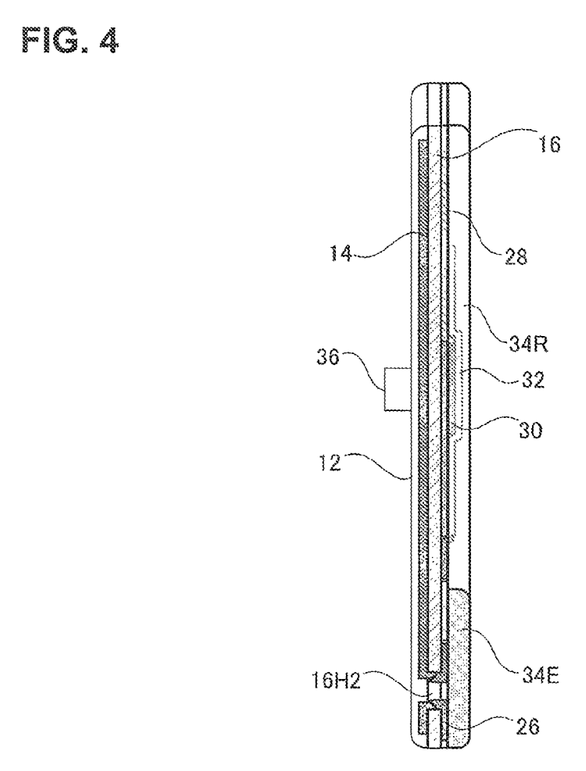
FIG. 4 shows a cross sectional view along the line Y-Y in FIG. 2.

FIG. 4 is a cross sectional view along the line Y-Y in FIG. 2. This FIG. 4 shows firstly the connection structure of the electrode parts 20, the wiring parts 18, and the terminal parts 30 in the bioelectrode, secondary the connection structure between the shield layer 14 and the earth connection part 26 through the through hole 82H2 formed to the base material 16, and tertiary the connection structure between the earth connection part 26 and the third electrolyte layer region 34E in the electrolyte layers 34. In this FIG. 4, the connection structure of the electrode parts 20, the wiring parts 18, and the terminal parts 30 is substantially the same as in FIG. 3 above, and therefore the explanation thereof is omitted by using the same referential numbers, respectively.

Particularly in this FIG. 4, in the bottom side of the base material 16, the through hole 28H2 is formed, which penetrates through the material in the thickness direction. When the shield layer 14 is formed on the inner wall of this throughhole 28H2 by screen printing and the like, the carbons forming the shield layer 14 are adhered thereon. On the other hand, when the earth connection part 26 is formed by screen printing and the like on the surface facing to the biological body (the body side) of the base material 16, the electrically conductive material (e.g., silver) forming the earth connection part 26 is also adhered on the inner wall surface of the throughhole 28H2 to contact with said carbons above. Whereby, the electric connection between the shield layer 14 and the earth connection part 26 is implemented through the throughhole. Therefore, as obvious seen from this FIG. 4, the shield layer 14 is short circuited through the earth connection part 26, and the third electrolyte layer region 34E to the biological body.

However, the shield layer 14 can somewhat eliminate noises outside the biological body without specific earth connection with the biological body. Therefore, when the shield layer 14 is not earth-connected to the biological body, there is no need to provide the throughhole 28H2 to the base material 16, or to form the earth connection part 26.

Figure 5:
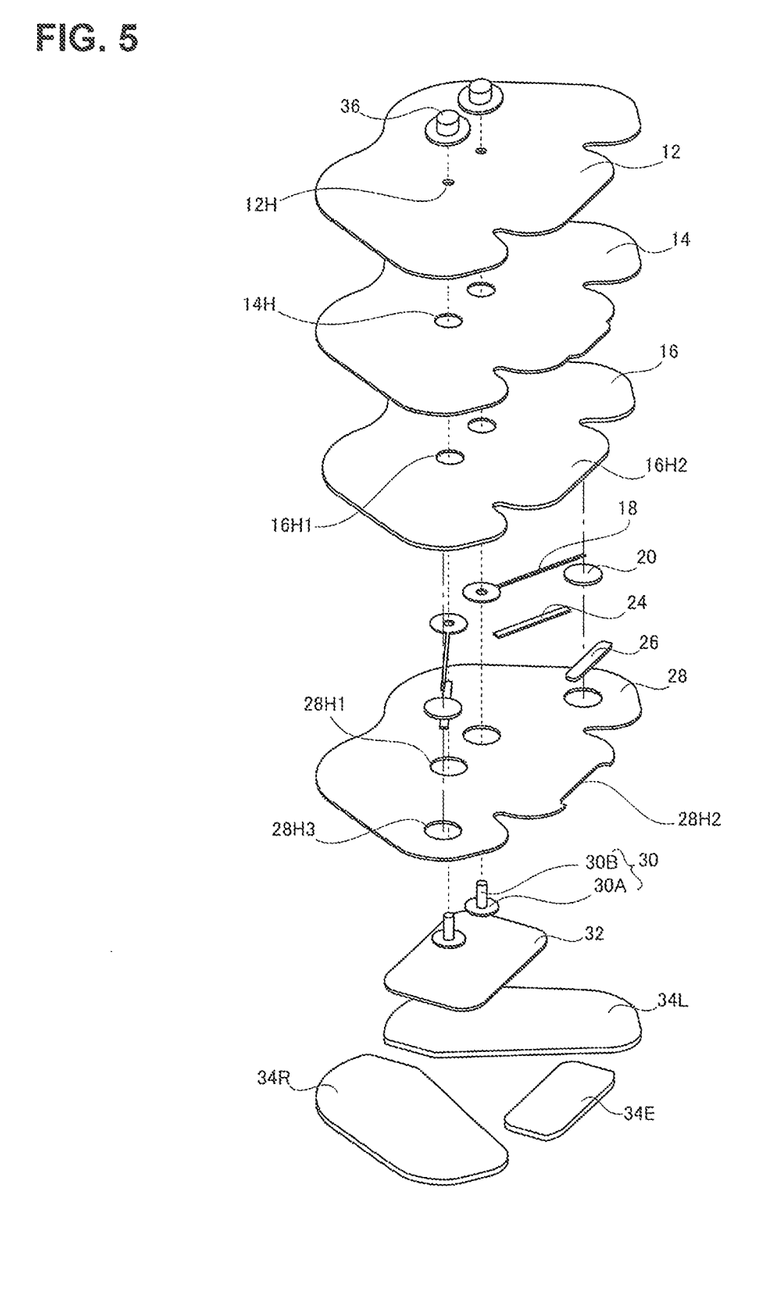
FIG. 5 shows an exploded perspective view of a bioelectrode of another embodiment according to the invention.

FIG. 5 is an exploded perspective view of a bioelectrode applying another configuration for the earth connection of the shield layer 14 to the biological body. Particularly in this embodiment, the bottom part of the shield layer 14 is formed such that said part is longer than the base material 16, and the earth connection part 26 comprised by the electrically conductive material is formed at the edge of the bottom part of the surface side on which the electrode parts 20 are provided in the base material 16. This earth connection part 26 can be also formed by printing or applying the electrically conductive material. In this embodiment the electrolyte holding part 28 has insulation property, and is provided to the area except for the region where the earth connection part 26 is present. As a result, the earth connection part 26 can closely contact with the third electrolyte layer region 34E in the electrolyte layers 34.

Figure 6:
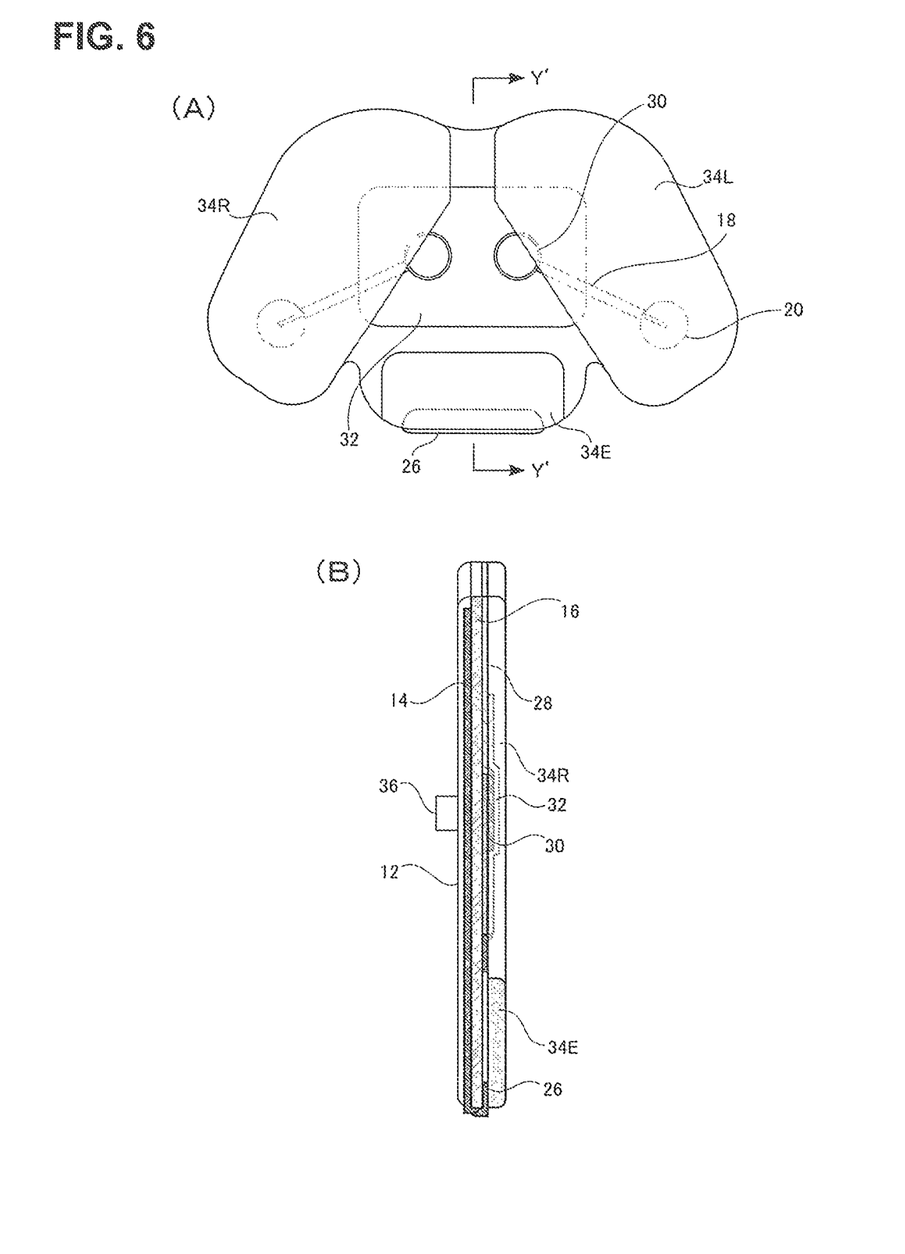
FIG. 6 shows a back view (A) and a cross sectional view along the line Y'-Y' of the bioelectrode of said another embodiment according to the invention.

In the bioelectrode formed in this way, as shown in FIG. 6(A), the earth connection part 26 is present in the bottom part of the surface of the biological body side of the bioelectrode, and said earth connection part 26 is covered by the third electrolyte layer region 34E. As shown in FIG. 6(B), the shield layer 14 formed so as to have a longer bottom side is wrapping around the side surface of the bottom part to present thereon by printing or applying the electrically conductive material. On the other hand, since, for the earth connection part 26, the electrically conductive material comprising this is also printed or applied such that said material wraps around the side surface of the bottom part of the base material 16, the shield layer 14 and the earth connection part 26 are electrically connected with each other on the side surface of the bottom part of the base material 16. Whereby, the shield layer 14 can be earth-connected to the biological body, and thus the potential of the shield layer 14 can be stabilized.

Figure 7:
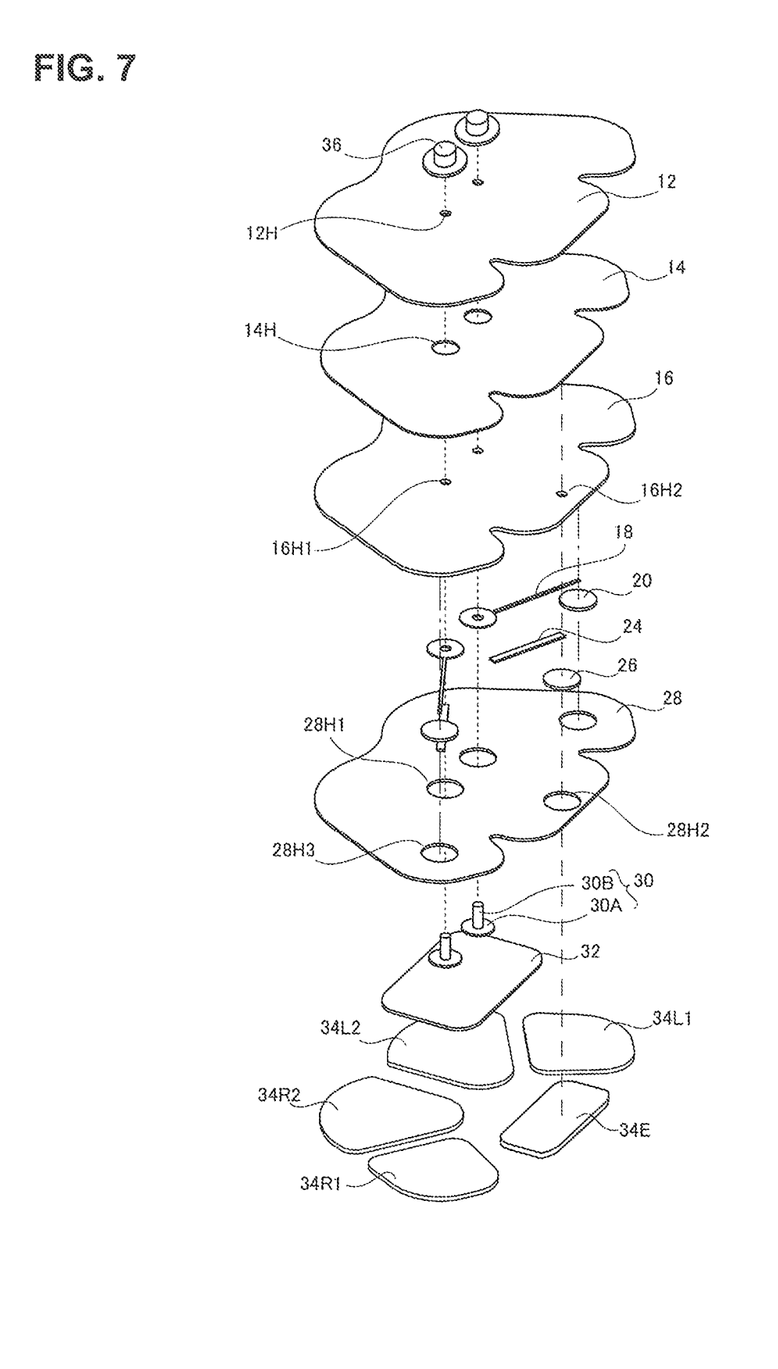
FIG. 7 shows an exploded perspective view of a bioelectrode of yet another embodiment according to the invention.
Figure 8:
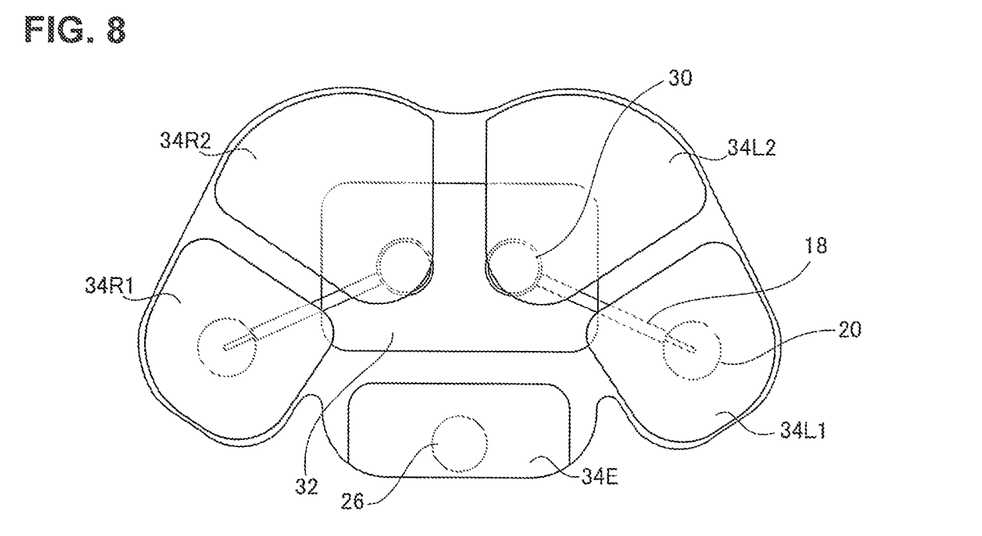
FIG. 8 shows a back view of the bioelectrode of said yet another embodiment according to the invention.

Another embodiment of the bioelectrode will be explained with reference to FIGS. 7 and 8 below. FIG. 7 is an exploded perspective view of a bioelectrode of another embodiment of the bioelectrode, and FIG. 8 is a back view of said bioelectrode. In the bioelectrode of this embodiment, the configuration of the electrolyte layers is particularly different from that of the bioelectrode shown in FIGS. 1 and 2 above. Since the components of the bioelectrode, other than said configuration of the electrolyte layer, are the same as those of FIGS. 1 and 2, any detailed explanation of such components with the same referential numbers is omitted.

More specifically, in the bioelectrode of this embodiment, each of the electrode parts are individually covered by discrete electrolyte layers, and therefore, each of the electrolyte regions covering the respective electrode parts are not electrically connected each other. More specifically, the bioelectrode comprises a first electrode electrolyte layer region 34R1 covering one electrode part 20 present in one side of the base material 16 in the width direction, and a second electrode electrolyte layer region 34L1 covering the other electrode part 20 present in the other side of the base material 16 in the width direction. Then, this first electrode electrolyte layer region 34R1 and the second electrode electrolyte layer region 34L1 are not electrically connected each other.

Furthermore, in this embodiment, to the upper area of the first electrode electrolyte layer region 34R1, a first electrolyte region of upper side 34R2 is provided, and a second electrolyte layer region of the upper side 34R2 is provided to the upper area of the second electrode electrolyte layer region 32L1. The first electrolyte region of upper side 34R2 and the second electrolyte layer region of the upper side 34L2 are used for the adhesion of this bioelectrode to the biological body, and therefore, they are formed so as to have at least adhesive property. Since these first electrolyte region of upper side 34R2 and second electrolyte layer region of the upper side 34L2 are not for obtaining any biological signal, they are not necessary to be electrically conductive.

Moreover, the first electrolyte region of upper side 34R2 and the second electrolyte layer region of the upper side 34L2 can be connected with each other, or formed into a unified form. However, it is desirable that no electrolyte is present in the lower area of the edge of the upper side, as shown in the embodiment, in order to adsorb any deformation of the base material depending on the body motion by bending the regions including the lines connecting the notches formed at the upper and the lower edges of the base material.

As shown in the embodiments of the invention, by forming the area surface of the electrolyte covering the electrode parts so as to be twice to 15 times, preferably, 7 times to 13 times of the electrode parts, the targeted biological signals can be adequately obtained. For example, when electrocardiogram signals are obtained, noises of myoelectric signals can be reduced.

The larger the area surface of the electrolyte layer connected to each of the electrode parts is, the larger the derived voltage for the electrocardiogram can be taken, as well as, the electromyogram at the same time. As a result of the derivation of the electrocardiogram and the electromyogram together, some voltage could be compensated to lower the output voltage from the electrodes. In order to take a large electrocardiogram voltage, the electrolyte layer remains only the periphery of the electrode parts, and the rest region is used for the adhesive connection of the bioelectrode to the biological body. Whereby, even though this is a one-channel bioelectrode, the bioelectrode is of high-output, and about twice electrocardiogram voltage, as compared with the conventional bioelectrodes, can be obtained. Moreover, as combined with the effect by the shield layer, the S/N ratio can be predominantly improved.

In the embodiments above, though a bioelectrode of two-electrode, having a "M"-like shape, i.e., a spread-toward-the bottom-shape, of the base material 16 has been illustrated, the materials and shapes for any layer or any part may be appropriately changed without departing from the scope of the invention.

INDUSTRIAL APPLICABILITY

The bioelectrode according to the invention can be used in a portable (wearable) biological information processing device, or other biological information acquisition device. As well, the bioelectrode of the invention can be used as a bioelectrode which can be attached by a user oneself to the user's body.

EXPLANATION OF REFERENTIAL NUMBERS

12: cover film,
14: shield layer,
16: base material,
18: wiring part,
20: electrode part,
24: insulating part,
26: earth connection part,
28: electrolyte holding part,
28H2: through hole,
30: terminal part,
34: electrolyte layer,
34L: first electrolyte layer region,
34R: second electrolyte layer region,
34E: third electrolyte layer region, and
36: stud.

What we claim is:
1. A bioelectrode used for transmitting electric stimulations to a biological body, for sensing electric signals from a biological body, or for both, by contacting said bioelectrode to the biological body, characterized in that said bioelectrode comprises:
   a base material formed into a sheet-shape;
   electrode parts provided on any one surface of said base material;
   an electrolyte layer comprising first and second electrolyte layer regions covering said electrode parts;
   terminal parts exposed on the surface opposed to the surface on which said electrode are provided, being electrically connected with said electrode parts, wherein said base material is shaped in a form having an upper part and a bottom part wider than the upper part, so called a spread-toward-the bottom-shape, and wherein said respective electrode parts are placed at positions near the bottom of said base material with predetermined distances in the width direction of the base material, wherein two electrode parts are provided, each is provided at a position near the edge of the base material in the width direction thereof, wherein two terminal parts are provided in non-adjoining, side by side relationship in the width direction of the base material at a position near the center of said base material in the width direction thereof, wherein, in each of areas of one side and the other side in the width direction of said base material, a respective terminal part and a respective electrode part are electrically connected by a wiring part, and wherein the first electrolyte layer region covers one pair of the electrode and the wiring part in the width direction of the base material, the second electrolyte layer region covers another pair of the electrode part and the wiring part in the width direction of the base material; the first and second electrolyte layer regions not being electrically connected with each other.

2. A bioelectrode used for transmitting electric stimulations to a biological body, for sensing electric signals from a biological body, or for both, by contacting said bioelectrode to the biological body, characterized in that said bioelectrode comprises:

a base material formed into a sheet-shape;

electrode parts provided on any one surface of said base material;

an electrolyte layer comprising a plurality of electrolyte layer regions covering said electrode parts;

terminal parts exposed on the surface opposed to the surface on which said electrode parts are provided, being electrically connected with said electrode parts, wherein said base material is shaped in a form having an upper part and a bottom part wider than the upper part, so called a spread-toward-the bottom-shape, and wherein said respective electrode parts are placed at positions near the bottom of said base material with predetermined distances in the width direction of the base material, wherein said terminal parts comprise flat surface parts present on the surface side of the base material on which the electrode parts are provided, and axes parts projecting from said flat surface parts, and passing through the base material, wherein said terminal parts and the electrode parts are electrically connected by wiring parts, and wherein said wiring parts are formed by printing or applying an electrically conductive material to electrically connect said electrode parts and the flat surface parts of said terminal parts.

3. A bioelectrode used for transmitting electric stimulations to a biological body, for sensing electric signals from a biological body, or for both, by contacting said bioelectrode to the biological body, characterized in that said bioelectrode comprises:

a base material formed into a sheet-shape;

electrode parts provided on any one surface of said base material;

an electrolyte layer comprising first, second and third electrolyte layer regions for covering said electrode parts;

terminal parts exposed on the surface opposed to the surface on which said electrode parts are provided, being electrically connected with said electrode parts, wherein said base material is shaped in a form having an upper part and a bottom part wider than the upper part, so called a spread-toward-the bottom-shape, and wherein said respective electrode parts are placed at positions near the bottom of said base material with predetermined distances in the width direction of the base material, wherein said terminal parts and the electrode parts are electrically connected by wiring parts, wherein a shield layer comprised by an electrically conductive material is provided on the surface side where the terminal parts are present in said base material, wherein said third electrolyte layer region is not electrically connected with said first electrolyte layer region and the second electrolyte layer region, and wherein said shield layer is electrically connected with said third electrolyte region.

4. A bioelectrode used for transmitting electric stimulations to a biological body, for sensing electric signals from a biological body, or for both, by contacting said bioelectrode to the biological body, characterized in that said bioelectrode comprises:

a base material formed into a sheet-shape;

electrode parts provided on any one surface of said base material;

an electrolyte layer comprising first, second and third electrolyte layer regions for covering said electrode parts;

terminal parts exposed on the surface opposed to the surface on which said electrode parts are provided, being electrically connected with said electrode parts, wherein said base material is shaped in a form having an upper part and a bottom part wider than the upper part, so called a spread-toward-the bottom-shape, and wherein said respective electrode parts are placed at positions near the bottom of said base material with predetermined distances in the width direction of the base material, wherein said first electrolyte layer region and said second electrolyte layer region are provided with a distance between them on the surface side on which the electrode parts are provided in the base material, wherein said third electrolyte layer region, which is not electrically connected with the first electrolyte layer region and the second electrolyte layer region, is provided between said first electrolyte layer region and said second electrolyte layer region, wherein said base material has one notch at the upper edge side, and two notches at the lower edge side, and wherein at least said electrode parts are provided in an area except for regions including lines connecting the notch at the upper edge side and each of the notches at the lower edge side of the base material.

5. A bioelectrode used for transmitting electric stimulations to a biological body, for sensing electric signals from a biological body, or for both, by contacting said bioelectrode to the biological body, characterized in that said bioelectrode comprises:

a base material formed into a sheet-shape;

electrode parts provided on any one surface of said base material;

an electrolyte layer comprising first, second and third electrolyte layer regions for covering said electrode parts;

terminal parts exposed on the surface opposed to the surface on which said electrode parts are provided, being electrically connected with said electrode parts, wherein said base material is shaped in a form having an upper part and a bottom part wider than the upper part, so called a spread-toward-the bottom-shape, and wherein said respective electrode parts are placed at positions near the bottom of said base material with predetermined distances in the width direction of the base material, wherein said third electrolyte layer region is not electrically connected to said first electrolyte layer region and said second electrolyte layer region, wherein a shield layer comprised by an electrically conductive material is provided on the surface side where the terminal parts are present, wherein an earth connection part formed by printing or applying an electrically conductive material is present within the area where said third electrolyte layer region is present on the surface side on which the electrode parts are provided in said base material, and wherein said earth connection part is electrically connected to said shield layer, and contacted with said third electrolyte region.

* * * * *